(12) United States Patent
Weber

(10) Patent No.: US 7,632,299 B2
(45) Date of Patent: Dec. 15, 2009

(54) MEDICAL DEVICES

(75) Inventor: Jan Weber, Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 866 days.

(21) Appl. No.: 10/762,815

(22) Filed: Jan. 22, 2004

(65) Prior Publication Data

US 2005/0165470 A1    Jul. 28, 2005

(51) Int. Cl.
*A61F 2/06* (2006.01)

(52) U.S. Cl. .................................... 623/1.15

(58) Field of Classification Search ............... 623/1.15, 623/1.16, 1.18, 1.2, 1.22, 1.46, 1.49; 606/191–198
See application file for complete search history.

(56) References Cited

U.S. PATENT DOCUMENTS

| | | |
|---|---|---|
| 4,655,771 A | 4/1987 | Wallsten |
| 5,163,952 A | 11/1992 | Froix |
| 5,195,969 A | 3/1993 | Wang et al. |
| 5,258,020 A | 11/1993 | Froix |
| 5,270,086 A | 12/1993 | Hamlin |
| 5,366,504 A | 11/1994 | Anderson et al. |
| 5,607,467 A | 3/1997 | Froix |
| 5,665,114 A | 9/1997 | Weadock et al. |
| 5,674,242 A | 10/1997 | Phan et al. |
| 5,954,744 A | 9/1999 | Phan et al. |
| 6,168,619 B1 | 1/2001 | Dinh et al. |
| 6,248,129 B1 | 6/2001 | Froix |
| 6,340,367 B1 * | 1/2002 | Stinson et al. ............. 623/1.34 |
| 6,530,950 B1 | 3/2003 | Alvarado et al. |
| 6,585,755 B2 | 7/2003 | Jackson et al. |
| 6,585,758 B1 * | 7/2003 | Chouinard et al. ......... 623/1.16 |
| 6,653,426 B2 | 11/2003 | Alvarado et al. |
| 6,770,089 B1 | 8/2004 | Hong et al. |
| 2003/0003220 A1 | 1/2003 | Zhong et al. |
| 2003/0004563 A1 | 1/2003 | Jackson et al. |
| 2003/0018380 A1 | 1/2003 | Craig et al. |
| 2003/0135265 A1 | 7/2003 | Stinson |
| 2003/0212449 A1 | 11/2003 | Cox |

FOREIGN PATENT DOCUMENTS

EP    1 258 229    11/2002

OTHER PUBLICATIONS

International Search Report received in Application No. PCT/US2005/000314, mailed May 6, 2005.

Sundback et al., "In Vitro and in Vivo Biocompatibility Analysis of Poly (Glycerol Sebacate) as a Potential Nerve Guide Material," www.mrs.org/meetings/fall2003/program/AbstractBookF.pdf, Abstract F.411.

Rumpf et al., "Fabrication and Characterization of Freestanding NiMnGa Thin Films," www.mrs.org/meetings/fall2003/program/AbstractBookD.pdf, Abstract D7.2.

(Continued)

*Primary Examiner*—Kevin T Truong
(74) *Attorney, Agent, or Firm*—Fish & Richardson P.C.

(57) ABSTRACT

Expandable stents and methods of using expandable stent within a body are described.

42 Claims, 4 Drawing Sheets

OTHER PUBLICATIONS

Labarre, "Improving Blood-Compatibility of Polymeric Surfaces", *Trends Biomater. Artif. Organs*, 15(1):1-3 (2001).

Bae et al., "Synthesis and Characterization of Heparinized Polyurethanes Using Plasma Glow Discharge", *Biomaterials*, 20: 529-537 (1999).

* cited by examiner

MEDICAL DEVICES

TECHNICAL FIELD

The invention relates to medical devices, such as stents and stent-grafts.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents and covered stents, sometimes called "stent-grafts".

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly.

One method of monitoring a medical device is magnetic resonance imaging (MRI). MRI is a non-invasive technique that uses a magnetic field and radio waves to image the body. In some MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body.

A device positioned within a patient's body is visible by MRI when the device has a sufficient contrast to noise ratio under MRI. For example, a sufficient contrast to noise ratio (e.g., greater than about 3) may allow a user to define an edge of a device.

SUMMARY

The invention relates to medical devices.

In one aspect, the invention features an expandable stent including a polymer wire extending spirally in a first direction about a longitudinal axis of the stent and a metal wire extending spirally in a second direction about the longitudinal axis, wherein the second direction is counter to the first direction.

Embodiments may include one or more of the following features. The polymer wire forms a first angle with the longitudinal axis and the metal wires forms a second angle with the longitudinal axis, wherein the first angle is equal to the second angle. The first angle can be different than the second angle. The first angle can be less than 35 degrees. The second angle can be between about 35 degrees and about 90 degrees. In certain embodiments the second angle can be between about 60 degrees and about 85 degrees.

The metal wire does not form a closed loop within the expandable stent. The metal wire can be visible on a magnetic resonance image. The metal wire can include a shape memory material, such as for example, a titanium alloy. The metal wire can have an oval cross-sectional area. The stent can include a plurality of metal wires spirally extending along the second direction.

The stent can include a plurality of polymer wires spirally extending along the first direction. The stent can also include a wire including a shape memory material spirally extending along the first direction.

The polymer wire can be substantially parallel to the longitudinal axis. The polymer wire can include polyethylene, such as a high density polyethylene. The polymer wire can have a modulus of elasticity between about 10 GPa and about 80 GPa. The polymer wire can have a tensile strength of about 1.2 GPa. To increase the biocompatibility of the polymer wire, the polymer wire can be treated with a plasma, such as a cold oxygen plasma. The polymer wire can be coated with a plastic.

The stent can further include a bioabsorable material including a drug on a surface of the stent. The bioabsorable material can be on an outer surface of the stent. The bioabsorable material can be on an inner surface of the stent.

The stent can be self expandable.

In another aspect, the invention features an expandable stent including a polymer wire extending substantially parallel to a longitudinal axis of the stent and a metal wire extending substantially perpendicular to the longitudinal axis, wherein the metal wire contacts the polymer wire.

Embodiments may include one or more of the following features. The metal wire can have a sinusoidal shape. The metal wire can be formed into a C shape. The metal wire can be visible on a magnetic resonance image. The metal wire can be formed into a ring. The stent can include a plurality of metal wires extending substantially perpendicular to the longitudinal axis. The plurality of metal wires can include a first metal wire including a first metal and a second metal wire including a second metal, wherein the first metal differs from the second metal.

The polymer wire can include polyethylene, such as for example, a high density polyethylene. The polymer wire can include a biodegradable polymer. The polymer wire can further include a drug within the biodegradable polymer. To increase the biocompatibility of the polymer wire, the polymer wire is treated with a plasma, such as for example, a cold oxygen plasma. At least a portion of the polymer wire can be coated with a plastic.

The stent can include a plurality of polymer wires, for example four polymer wires, six polymer wires, 8 polymer wires, or more, extending parallel to the longitudinal axis. The plurality of wires can include an inner wire positioned on an inner surface of the stent and an outer wire positioned on an outer surface of the stent. The inner wire can be fused to the outer wire. In certain embodiments, the polymer wire can include an aperture and the metal wire is positioned within the aperture.

The stent can be a balloon expandable stent.

In another aspect, the invention features an expandable stent including a polymer wire and a metal wire contacting the polymer wire, wherein the polymer wire is arrange such that substantially no plastic deformation of the polymer wire occurs during expansion of the stent and the metal wire is arranged to axially strengthen the expandable stent.

Embodiments may have one or more of the following features. The stent can be self expandable. The stent can be balloon expandable.

The metal wire does not form a closed loop within the stent. The metal wire is visible on a magnetic resonance image. The metal wire can include titanium, such as, for example a titanium alloy. The metal wire can have an oval cross-sectional area.

The polymer wire can be substantially parallel to a longitudinal axis of the stent. The polymer wire can include polyethylene, such as for example, a high density polyethylene. The polymer wire can include a biodegradable polymer. The polymer wire can further include a drug in the biodegradable polymer. The polymer wire can be treated with a plasma. A portion of the polymer wire can be coated with a plastic.

In another aspect, the invention features an expandable stent including a polymer member extending spirally in a first direction about a longitudinal axis of the expandable stent, and a metal member extending spirally in a second direction about the longitudinal axis, the second direction being counter to the first direction.

Embodiments may include one or more of the following features. The metal member includes a shape memory material. The polymer member forms a first angle with the longitudinal axis and the metal member forms a second angle with the longitudinal axis, the first angle being equal the second angle. The polymer member forms a first angle with the longitudinal axis and the metal member forms a second angle with the longitudinal axis, the first angle being different than the second angle. The polymer member is substantially parallel to the longitudinal axis. The metal member does not form a closed loop within the expandable stent.

In another aspect, the invention features an expandable stent including a polymer member extending substantially parallel to a longitudinal axis of the expandable stent, and a metal member extending substantially perpendicular to the longitudinal axis, the metal member contacting the polymer member.

Embodiments may include one or more of the following features. The metal member has a sinusoidal shape, a C shape, or a ring shape. The stent further includes a plurality of metal members extending substantially perpendicular to the longitudinal axis. The polymer member includes a biodegradable polymer. The stent further includes a plurality polymer members extending substantially parallel to the longitudinal axis.

In another aspect, the invention features an expandable stent including a polymer member and a metal member contacting the polymer member, wherein the polymer member is arranged such that substantially no plastic deformation of the polymer member occurs during expansion of the expandable stent and the metal member is arranged to axially strengthen the expandable stent. In embodiments, the metal member does not form a closed loop within the expandable stent.

Embodiments may have one or more of the following advantages. The medical device can include a metal element and a polymer element that together provide relatively good mechanical strength and at the same time do not compromise the MRI visibility of the medical device. For example, the mechanical strength of the medical device including metal elements and polymer elements allows for expansion and/or contraction of the device without reducing the device's capability to reinforce a body lumen. Moreover, a medical professional can use MRI techniques to position and monitor the device because the metal elements and the polymer elements are arranged within the device so that the metal elements do not produce artifacts that interfere with MRI visibility. A medical device including metal elements and polymer elements can be either self expanded or balloon expanded without losing the device's elastic properties. As a result, the medical device can be repeatedly expanded and contracted. As a further result, the expanded medical device maintains the mechanical strength required to reinforce a body lumen.

Other aspects, features and advantages of the invention will be apparent from the description of the preferred embodiments and from the claims.

DETAILED DESCRIPTION

Figure 1:
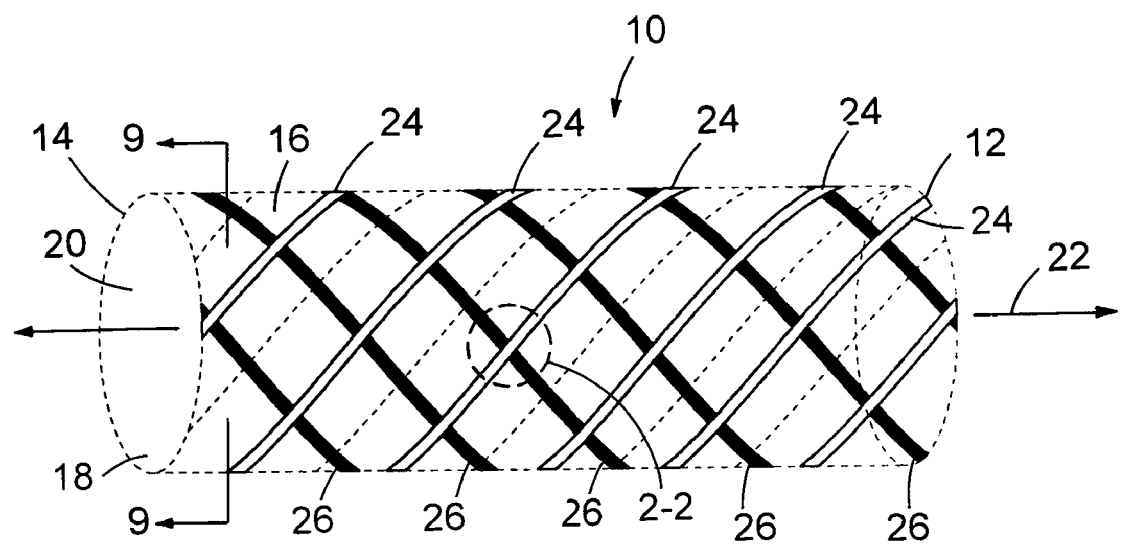
FIG. 1 is an illustration of a stent in a compacted state.

Referring to FIG. 1, an MRI-compatible stent 10 is formed of a composite structure including a plurality of metal wires 24 and a plurality of electrically non-conductive polymer wires 26. Wires 24 and 26 are braided or woven, e.g., as described in Wallsten, U.S. Pat. No. 4,655,771, and extend between the ends 12 and 14 of the stent to define a lumen 20. As shown, metal wires 24 extend spirally in a first direction about the longitudinal axis 22 of stent 10 (e.g., clockwise as viewed from one end down the longitudinal axis), and polymer wires 26 extend spirally in an opposing direction (e.g., counter-clockwise as viewed from the same end) about the longitudinal axis. As described below, metal wires 24 provide stent 10 with good mechanical properties (e.g., sufficient to maintain a body lumen open), while allowing for visualization of material, such as blood or a stenosis, present in the lumen of the stent during MRI. Polymer wires 26 reduce the amount of metal wires used to form stent 10, thereby increasing the MRI compatibility of the stent, and can enhance the flexibility and strength of the stent.

In preferred embodiments, metal wires 24 are selected and arranged within stent 10 such that they do not adversely affect visualization during an MRI procedure, while providing the stent with its mechanical properties to function properly (i.e., the stent can be compacted to a reduced size and subsequently expanded to support a lumen). More specifically, metal wires 24 are formed such that an electrical current cannot flow in a closed loop about stent 10. Without wishing to be bound by theory, it is believed that the presence of an electrical current loop can interfere with MRI and reduce visualization.

During MRI, an incident electromagnetic field is applied to a stent. The magnetic environment of the stent can be constant or variable, such as when the stent moves within the magnetic field (e.g., from a beating heart) or when the incident magnetic field is varied. When there is a change in the magnetic environment of the stent, which can act as a coil or a solenoid, an induced electromotive force (emf) is generated, according to Faraday's Law. The induced emf in turn can produce an eddy current that induces a magnetic field that opposes the change in magnetic field. The induced magnetic field can interact with the incident magnetic field to reduce (e.g., distort) the visibility of material in the lumen of the stent. A similar effect can be caused by a radiofrequency pulse applied during MRI.

By forming stent 10 to include electrically conductive portions (as shown, wires 24) that cannot form a closed current loop, the occurrence of an eddy current is reduced (e.g., eliminated). Consequently, the occurrence of an induced magnetic field that can interact with the incident magnetic field is also reduced, and the visibility of material in the lumen of stent 10 during MRI can be enhanced.

Polymer wires 26 also enhance the performance of stent 10. Polymer wires 26, which are electrically non-conductive, do not interfere with MRI signals. Also, by forming stent 10 partially with polymer wires 26, the amount of metal wires 24 is reduced, thereby reducing the occurrence of static interference as an effect of the magnetic susceptibility of the metal wires. At the same time, polymer wires 26 can provide stent 10 with strength and flexibility.

Figure 2:
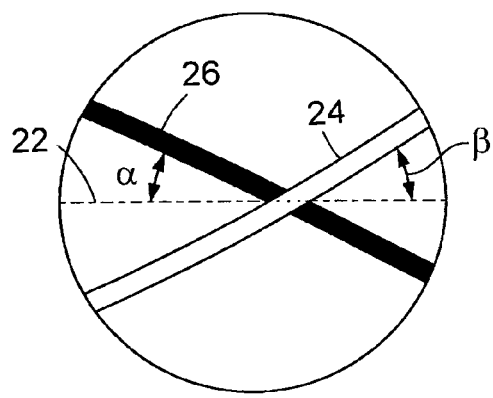
FIG. 2 is an enlarged view of a portion of the stent of FIG. 1, at area 2-2.
Figure 3:
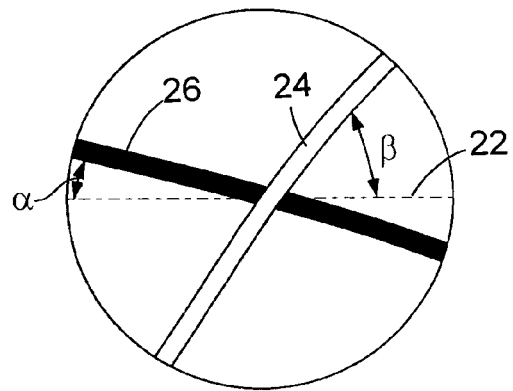
FIG. 3 is another enlarged view of a portion of a stent.

In some embodiments, polymer wires 26 are arranged such that they are not substantially plastically deformed during compaction and expansion of stent 10. Without wishing to be bound by theory, it is believed that as stent 10 is expanded, the majority of change in the stent's width and length, and thus most of the stress, occurs in the radial direction (e.g., perpendicular to longitudinal axis 22). By positioning polymer wires 26 to have a component along longitudinal axis 22, plastic deformation of polymer wires 26 can be reduced because the stress experienced by the polymer wires is proportional to their radial component. In certain embodiments, referring to FIGS. 2 and 3, polymer wires 26 form an angle of about 45° or less (e.g., $\leq 45°$, 40°, 35°, 30°, 25°, 20°, 15°, 10°, 5°, 0°) with longitudinal axis 22 (e.g., $0° \leq \alpha \leq 45°$ and thus can be substantially parallel with the longitudinal axis 22). In comparison, metal wires 24 can form an angle of 35° or greater (e.g., $\geq 35°$, 40°, 45°, 50°, 55°, 60°, 65°, 70°, 75°, 80°, 85°, 89°) with the longitudinal axis (e.g., $35° \leq \beta < 90°$, e.g., $60° \leq \beta \leq 85°$) and thus can be substantially perpendicular to the longitudinal axis 22). As a result, polymer wires 26 experience reduced stress associated with expansion and contraction and are therefore less likely to undergo plastic deformation. In addition, the stress exerted by a body lumen on an expanded stent is mainly in the radial direction. As a result, metal wires 24 counteract substantially all of the stress exerted by the lumen, thereby reducing the stress experienced by polymer wires 26.

In some embodiments, the angles that polymer wires 26 and/or metal wires 24 form can vary along the length of stent 10. For example, at the end portions of the stent, polymer wires 26 and/or metal wires 24 can form a first angle; and at the middle portion of the stent, the polymer wires and/or metal wires can form a second angle. The transitions of one angle to another angle can occur, for example, gradually over the length of the stent or step-wise, such that the stent has discrete segments of different angles form by the wire(s). The angles can be varied to affect the flexibility or rigidity of the stent. For example, the end portions of the stent can be relatively flexible to conform well with the contours of a body vessel, while the middle portion can be relatively rigid to support the vessel open.

Figure 4:
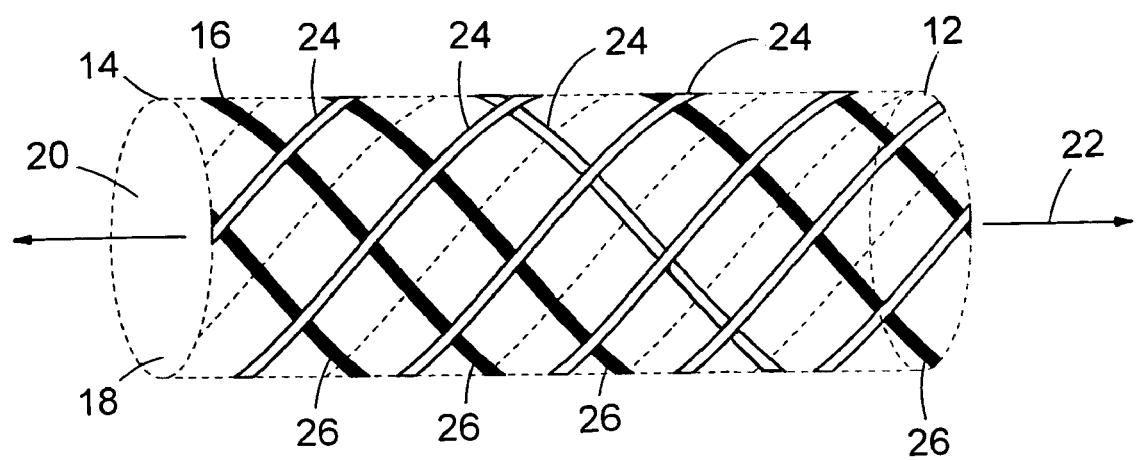
FIG. 4 is an illustration of a stent in a compacted state.

Other embodiments of stents having good MRI compatibility are possible. Referring to FIG. 4, one of the polymer wires 26 can be replaced with a metal wire as this design does not lead to closed conductive paths in the stent. In embodiments in which the stent is self expandable (e.g., metal wires include a shape memory material), the self expansion capabilities of the stent can be enhanced because the strength of the stent is increased by including an additional metal wire 24 that extends spirally in the counter-clockwise direction.

In other embodiments, the MRI visibility capabilities can be enhanced by replacing one or more (e.g., 1, 2, 3, 4, 5, 6, 7, 8 or more) of the metal wires 24 with polymer wires 26. The number of metal wires that are replaced with polymer wires depends on the size and shape of the stent, and ultimately on the ability of the remaining metal wires to self expand the stent to an expanded state. It is believed that by reducing the total number of metal wires within stent 10, magnetic susceptibility disturbances generated by the stent in an MRI decrease, while the contrast to noise ratio increases to provide increased MRI visibility.

Figure 5:
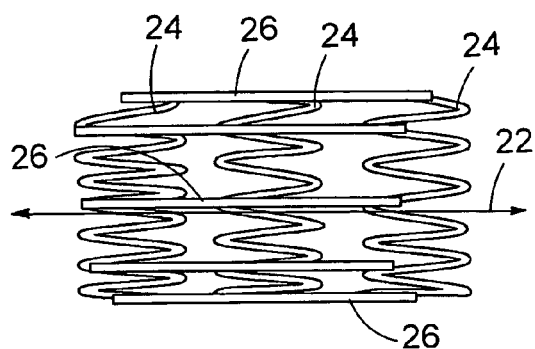
FIG. 5 is an illustration of a stent in a compacted state.
Figure 6:
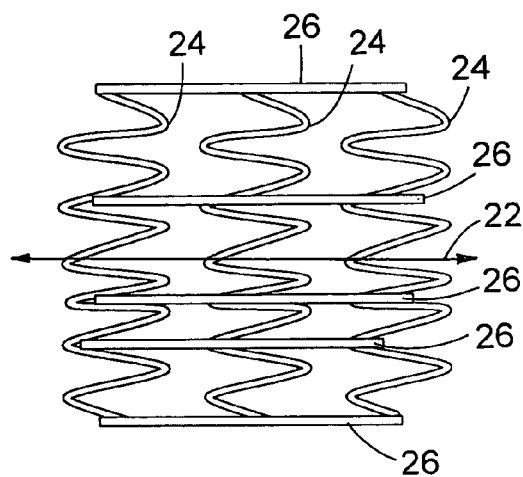
FIG. 6 is an illustration of the stent of FIG. 5 in an expanded state.

In other embodiments, referring to FIGS. 5 and 6, the one or more polymer wires 26 can extend substantially parallel to longitudinal axis 22 (e.g., $\alpha = 0°$) and the one or more metal wires can extend substantially perpendicular to longitudinal axis 22 (e.g., $\beta = 90°$). Since polymer wire(s) have a limited (e.g., substantially none) radial component, the polymer wire(s) undergo little plastic deformation during compaction and expansion of the stent. Conversely, metal wire(s) 24 have a large radial component to provide the stent with sufficient mechanical properties to support a body lumen. At least one of the metal wires 24 can have a sinusoidal shape, so as to provide additional surface contact between an expanded stent 10 and a patient's body lumen. In the embodiments shown in FIGS. 5-8, one or more polymer wires 26 (e.g., 1, 2, 3, 4, 5, 6, 7, 8 or more) hold the metal wires 24 together. For example, a mechanical connection between the polymer wires 26 and the metal wires 24 can be created by inserting the metal wires 26 through holes punched into the polymer wires 26. The mechanical connection can also be created by replacing each polymer wire 26 with two polymer wire strips, one in contact with the outer surface 16 and one in contact with the inner surface 18, and fusing the polymer wire strips together to encapsulate a portion of each metal wire 26.

Figure 8:
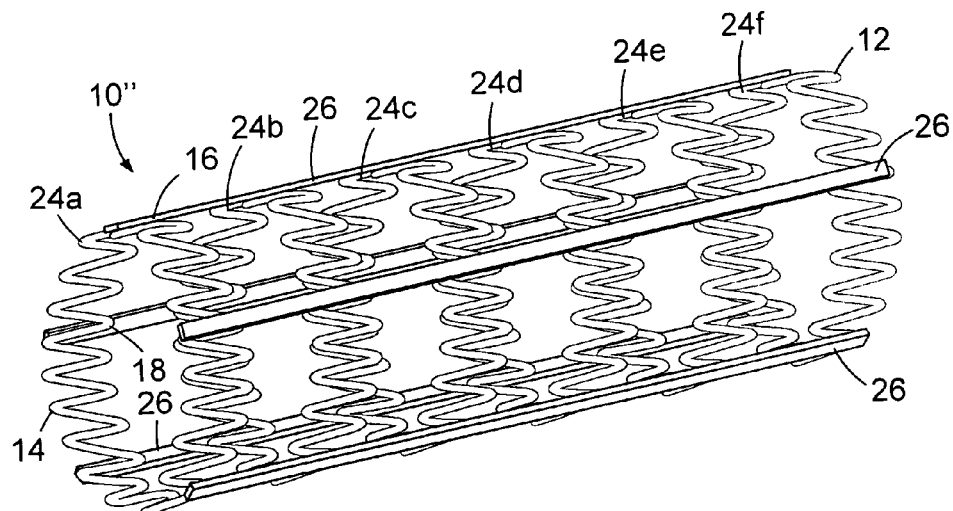
FIG. 8 is a perspective view of a stent.
Figure 7:
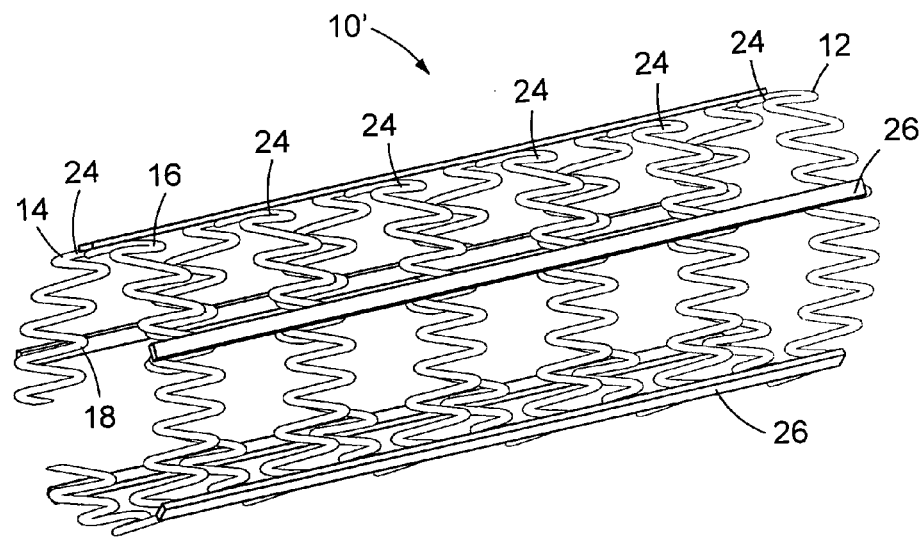
FIG. 7 is a perspective view of a stent.

As shown in FIGS. 7 and 8, each metal wire 24 can be formed in a "C" shape (FIG. 7) or in a ring shape (FIG. 8). Stents, such as stent 10', which include "C" shaped metal wires (i.e., metal wires 24 do not create a continuously conductive circuit in a plane perpendicular to longitudinal axis 22) do not interfere with MRI visualization as described above. However, stents 10" that include ring shaped metal wires, such as the stent shown in FIG. 8, may interfere with MRI visualization, but may be useful when view or monitored using fluoroscopic techniques. Accordingly, in some embodiments, the rings are formed of a metal (e.g., gold, silver, platinum) visible under fluoroscopy so that stent 10" can be visualized within a patient's body during delivery and placement. In certain embodiments, stent 10" includes one or more metal rings formed of a first material and one or more metal rings formed of a second material. For example, the metal wires labeled 24a and 24f in FIG. 8 can be formed of a metal that is more radio-opaque (creates a greater contrast under fluoroscopy) than the metal forming wires 24b, 24c, 24d and 24e. Additionally, adjacent rings can be formed of a material having a different radiopacity. For example, wires 24a, 24c, and 24e can be formed of a metal having a first radiopacity, and wires 24b, 24d, and 24f can be formed of a material having a second radiopacity.

The stents described above can be self-expanding, balloon expanding, or a combination of both (U.S. Pat. No. 5,366, 504), depending on the materials used. For balloon expandable stents, metal wires can include an elastic material that maintains its shape once plastically deformed. Examples of elastic materials include titanium, titanium alloys, tantalum, niobium, Co—Cr alloys, and alloys described in U.S. Ser. No. 10/112,391 filed on Mar. 28, 2002.

For self expandable stents, metal wires can include a shape memory material that expands and/or contracts as a result of a phase change. Examples of suitable shape memory materials include titanium alloys, such as for example a nickel titanium alloy (e.g., Nitinol), copper aluminum alloys, such as for example Cu—Zn—Al, Cu—Al—Ni, and Cu—Al, Fe—Mn—Si, Au—Ca, and $Ni_{50}Mn_{30}Ga_{20}$ ($Ni_{50}Mn_{30}Ga_{20}$ wires prepared from DC magnetron sputtered $Ni_{50}Mn_{30}Ga_{20}$ films that have been annealed on a glass plate). Typically, elastic and shape memory materials are flexible materials (e.g., modulus of elasticity is less than about 90 GPa) that have sufficient mechanical strength (e.g., ultimate tensile strength greater than 1 GPa) to reinforce a body lumen even after plastic deformation and/or a phase change.

Figure 9:
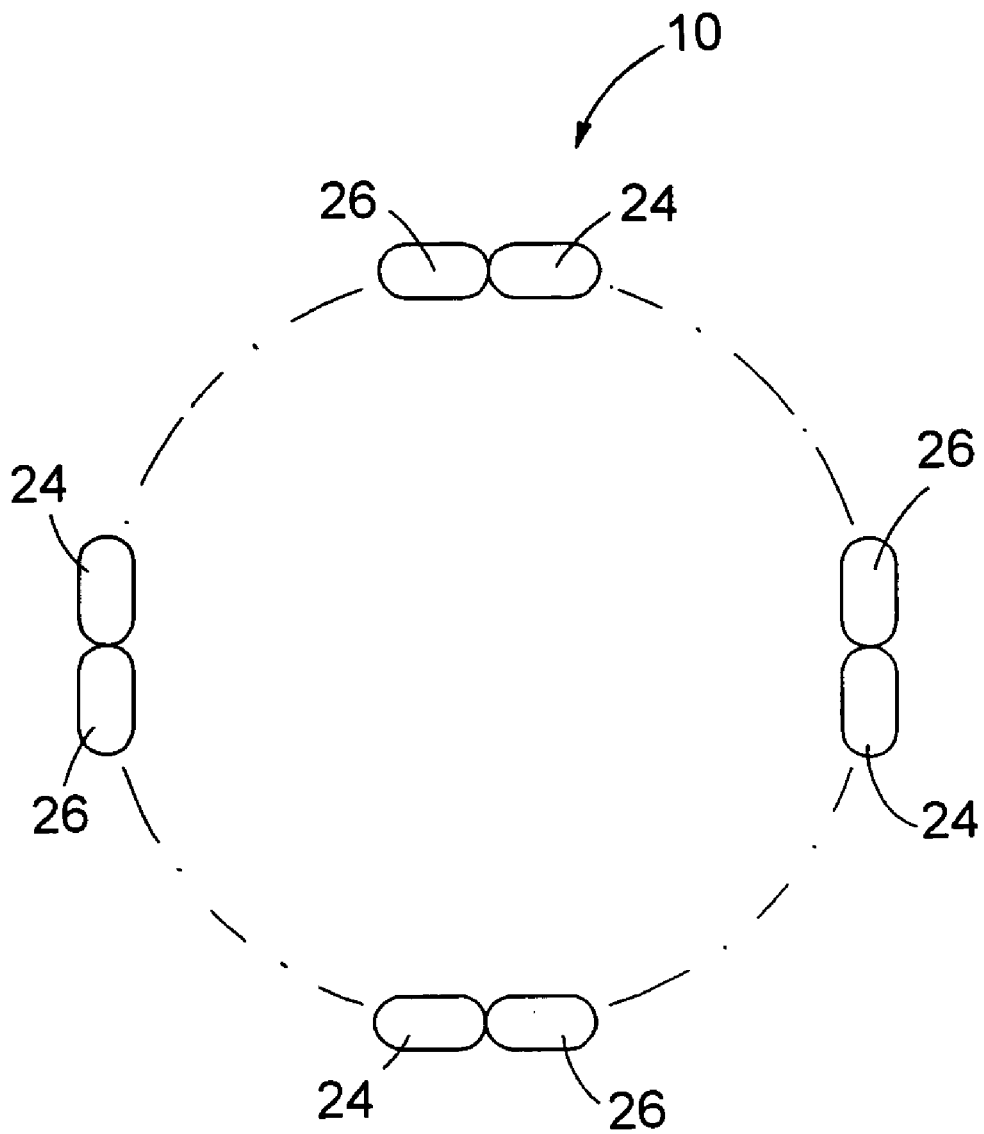
FIG. 9 is a cross-sectional view of the stent of FIG. 1 taken along line 9-9.

Metal wires can be molded or laser cut from a solid tube of material to have a spiral shape. The metal wires can have a cross-sectional area of about $2.5 \times 10^{-5}$ $cm^2$ to about $2.5 \times 10^{-3}$ $cm^2$. In certain embodiments, it is preferable to use a wire that has an oval cross-sectional shape so that the long diameter of the oval can be aligned with (i.e., substantially parallel to) the circumference of stent 10, as shown in FIG. 9. By aligning the long diameter with the circumference, the radial expansion force of the stent with respect to the amount of metal material used in stent 10 is increased (e.g., maximized). While an oval cross-sectional shape is preferable, metal wires 24 can have other cross-sectional shapes such as, for example, regularly or irregularly polygonal having three or more (e.g., 4, 5, 6, 7, 8 or more) sides, such as rectangular, square, circular, and triangular. Wires of different cross sections can be used in a stent.

Polymer wires used in either self expanding or balloon expanding stents include flexible and strong polymers that have suitable material properties to aid in body lumen reinforcement and at the same time also have material properties that do not compromise the MRI compatibility of the stent. Some examples of polymers include polyethylene, polyimide, polyamide, polycarbonate, polyetheretherketone, and polyethylene terephthalate.

In certain embodiments, polymer wires 26 are formed of a highly oriented polymer material, such as polyethylene (e.g., a high density polyethylene (HDPE) material formed using a solid-state extrusion process). The HDPE polymer can have an average molecular weight ($M_w$) of about 400,000 g/mol, and a molecular weight distribution (i.e., polydispersity) of about 3 to 7, for example, a polydispersity of about 5. The polymer can have a high molecular weight tail (e.g., 0-10% content of greater than about 1,000,000) to ensure the formation of extended chain crystals. A minimal amount (<0.1%) of low molecular weight (e.g., 4000 g/mol or less) fraction is preferred to prevent the premature onset of relaxation processes in the melt and to ensure force transfer during extrusion of the melt through a die. Low molecular weight fractions can be removed by extraction in an appropriate solvent (e.g., hexane) to increase the tensile module of the resulting fiber. Examples of HDPEs are commercially available from, e.g., BASELL (BASF) Corporation under the trade designation LUPULEN 52ZHI; Chevron Philips Corporation under the trade designation MARLEX TR-751; and Solvay Corporation under the trade designations RIGIDEX HM5420 XPH, AH 5493, and BH 5363.

A polymer wire can be prepared, for example, by extrusion. The cross-section of the polymer wire can be as described above for the metal wire. The polymer can be extruded to form relatively stiff fibers having the requisite mechanical properties (e.g., Young's modulus (E) of greater than about 10 GPa and a tensile strength of greater than about 1 GPa). HDPE fibers can be prepared by solid-state extrusion of melt crystallized spherulitic polyethylene or by drawing solution crystallized gel films (e.g., performed by DSM (Heerlen, The Netherlands) as a process marketed as the Dyneema® Process). An alternative process involves melt deformation of HDPE under controlled conditions to obtain highly oriented fibers. The process involves chain extension of the high molecular weight fraction of HDPE having a linear macromolecular stricture during flow just above the solidification temperature, followed by crystallization (e.g., of a high molecular weight fraction) and by co-crystallization e.g., of a low molecular weight fraction) of the remaining material. The polymer can be extruded at a temperature close to the crystallization temperature (e.g., a self-blocking temperature, which can be indicated by an extrusion pressure rise, e.g., upward from about 3500 psi) and at a strain rate of about 1000 $s^{-1}$ to solidify the deformed macromolecules before relaxation occurs. In some cases, crystallization occurs from about $T_g+30$ to about $T_m-10$ (e.g., from about 135 to about 160° C.). Such processing conditions can create an elongated, interlocking morphology that displays exceptional mechanical properties (e.g., a Young's modulus (E) of between about 10-80 GPa and a tensile strength of about 1.2 GPa). The fibrils can make up about 5% of the extruded material and can have a diameter of between about 5-25 nm with an aspect ratio of about 200-600. The bulk material can be characterized as a lamellar overgrowth chain direction like in the fibrils. An example of an extrusion apparatus is a mini-extruder (Axxon BX 12, D=12.5 mm, L/D=26) with a suitably designed die (e.g., opening angle 45°, 1 mm, 1/d 25). The extrusion head can be equipped with a pressure transducer and a thermocouple to control pressure and temperature during extrusion. Additional information regarding HDPEs is described in Bashir, Z., et al., *J. Mat. Science,* 19 (1984), 3713; and Bashir, Z., et al., *J. Mat. Science,* 19 (1986), 3993.

In some embodiments, the polymer wires 26 are extruded to have a preformed spiral shape. In other embodiments, the polymer wires 26 are molded at a temperature at or below their melting temperature to form the spiral shape.

In some embodiments, the HDPE fibers can be treated with a cold oxygen plasma to increase the biocompatibility of the fibers. Generally, by treating HDPE with a cold oxygen plasma, the hydrophylicity of the surface of the HDPE fibers increases, which results in increased biocompatibility. However, in order to minimize the likelihood of destruction of the interlocking morphology, and thus compromise the mechanical properties of the fibers, the cold oxygen plasma treatment preferably occurs at a temperature at or below the melting temperature of HDPE. An example of a suitable cold oxygen plasma technique with the required low temperature is a downstream microwave plasma technique. As the life expectancy of a plasma treated surface is only limited, it is preferable to provide a coating, such as for example a plastic coating (e.g., styrene-isobutylene-styrene and poly glycerol sebacate), on top of the plasma treated surface.

In some embodiments, the polymer wires 26 are formed of a biodegradable polymer material, such as for example, poly (L-lactid acid) that disintegrates over a period of time within the patient's body. Preferably the biodegradable polymer material does not disintegrate until at least a portion of the metal wires 24 are affixed to the patient's body lumen by tissue growth. The biodegradable polymer can include drugs, such as therapeutic agents or pharmaceutically active compounds that are released upon disintegration of the polymer wires. Examples of therapeutic agents and pharmaceutically active compounds include anti-thrombogenic agents, antioxidants, anti-inflammatory agents, anesthetic agents, anti-coagulants, and antibiotics. Other examples suitable therapeutic agents and pharmaceutically active compounds are described in U.S. Pat. No. 5,674,242, commonly assigned U.S. Ser. No. 09/895,415, filed Jul. 2, 2001, and U.S. Ser. No. 10/112,391, filed Mar. 28, 2002.

In other embodiments, stent 10 can include and/or be attached to a biocompatible, non-porous or semi-porous polymer matrix made of polytetrafluoroethylene (PTFE), expanded PTFE, polyethylene, urethane, or polypropylene.

In some embodiments, the polymer wires 26 can be coated and/or treated with an anti-coagulant, such as for example heparin, to increase the biocompatibility of stent 10, 10', and 10". Examples of methods of applying heparin to polymer surfaces are described in Labarre, *Trends. Biomater. Artif. Organs,* 15(1) (2001), 1, and Bae et al., *Biomaterials,* 20 (1999), 529.

In some embodiments, stents 10, 10' and 10" can include a bioabsorable material that includes a therapeutic agent and/or a pharmaceutically active compound disposed within the bioabsorable material. An example of a bioabsorable material including therapeutic agents is a polyelectrolyte (LBL) coating including layers of chitosan and heparin. The bioabsorable material can be positioned on outer surface 16 and/or inner surface 18 to treat the patient's body lumen.

Stents 10, 10' and 10" can be of any desired shape and size (e.g., coronary stents, aortic stents, peripheral stents, gastrointestinal stents, urology stents, and neurology stents). Depending on the application, stents 10, 10' and 10" can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

Stents 10, 10' and 10" can be used, e.g., delivered and expanded, using a balloon catheter system. Suitable catheter systems are described in, for example, Wang U.S. Pat. No. 5,195,969, and Hamlin U.S. Pat. No. 5,270,086. Suitable stent delivery are also exemplified by the Ranger® system, available from Boston Scientific Scimed, Maple Grove, Minn.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. An expandable stent, comprising:
   one or more polymer wires extending spirally in a first direction about a longitudinal axis of the expandable stent; and
   one or more metal wires extending spirally in a second direction about the longitudinal axis, the second direction being counter to the first direction, wherein the one or more metal wires intersect the one or more polymer wires at a plurality of intersection points, the one or more metal wires only intersecting the one or more polymer wires such that the one or more metal wires do not form a closed current loop, wherein the one or more metal wires have an oval cross-sectional area.

2. The expandable stent of claim 1, wherein the metal wire includes a shape memory material.

3. The expandable stent of claim 2, wherein the shape memory material comprises a titanium alloy.

4. The expandable stent of claim 1, further comprising a plurality of polymer wires spirally extending along the first direction.

5. The stent of claim 4, further comprising a wire comprising a shape memory material extending along the first direction.

6. The stent of claim 4, further comprising a plurality of metal wires spirally extending along the second direction.

7. The expandable stent of claim 4, wherein the plurality of polymer wires comprises four polymer wires.

8. The expandable stent of claim 4, wherein the plurality of polymer wires comprises six polymer wires.

9. The expandable stent of claim 4, wherein the plurality of polymer wires comprises eight polymer wires.

10. The expandable stent of claim 1, wherein the polymer wire comprises polyethylene.

11. The expandable stent of claim 1, wherein the polymer wire comprises high density polyethylene.

12. The expandable stent of claim 11, wherein the polymer wire is treated with a plasma.

13. The expandable stent of claim 1, wherein the polymer wire forms a first angle with the longitudinal axis and the metal wire forms a second angle with the longitudinal axis, the first being equal to the second.

14. The expandable stent of claim 1, wherein the polymer wire forms a first angle with the longitudinal axis and the metal wire forms a second angle with the longitudinal axis, the first angle being different than the second angle.

15. The expandable stent of claim 14, wherein the first angle is less than 35 degrees.

16. The expandable stent of claim 14, wherein the second angle is between about 35 degrees and about 90 degrees.

17. The expandable stent of claim 14, wherein the second angle is between about 60 degrees and about 85 degrees.

18. The expandable stent of claim 1, wherein the metal wire is visible on a magnetic resonance image.

19. The expandable stent of claim 1, further comprising a bioabsorbable material including a drug on the surface of the expandable stent.

20. The expandable stent of claim 19, wherein the surface is an inner surface of the expandable stent.

21. The expandable stent of claim 19, wherein the surface is an outer surface of the expandable stent.

22. The expandable stent of claim 1, wherein the expandable stent is self expandable.

23. The expandable stent of claim 1, wherein the polymer wire includes an aperture and the metal wire is positioned within the aperture.

24. The expandable stent of claim 1, wherein the expandable stent is balloon expandable.

25. The expandable stent of claim 1, wherein the polymer wire is arranged such that substantially no plastic deformation of the polymer wire occurs during expansion of the expandable stent and the metal wire is arranged to axially strengthen the expandable stent.

26. The expandable stent of claim 25, wherein the metal wire is visible on a magnetic resonance image.

27. The expandable stent of claim 25, wherein the expandable stent is self expandable.

28. The expandable stent of claim 25, wherein the expandable stent is balloon expandable.

29. The expandable stent of claim 25, wherein the metal wire comprises titanium.

30. The expandable stent of claim 25, wherein the metal wire comprises a titanium alloy.

31. The expandable stent of claim 25, wherein the polymer wire comprises polyethylene.

32. The expandable stent of claim 25, wherein the polymer wire comprises high density polyethylene.

33. The expandable stent of claim 32, wherein the polymer is treated with a plasma.

34. The expandable stent of claim 25, wherein at least a portion of the polymer wire is coated with a plastic.

35. The expandable stent of claim 25, wherein the polymer wire comprises a biodegradable polymer.

36. The expandable stent of claim 35, further comprising a drug in the biodegradable polymer.

37. An expandable stent, comprising:
one or more polymer wires extending spirally in a first direction about a longitudinal axis of the expandable stent, wherein the polymer wire has a tensile strength of about 1.2 GPa; and
one or more metal wires extending spirally in a second direction about the longitudinal axis, the second direction being counter to the first direction, wherein the one or more metal wires intersect the one or more polymer wires at a plurality of intersection points, the one or more metal wires only intersecting the one or more polymer wires such that the one or more metal wires do not form a closed current loop.

38. An expandable stent, comprising:
one or more polymer wires extending spirally in a first direction about a longitudinal axis of the expandable stent, wherein the one or more polymer wires comprise high density polyethylene treated with a plasma; and
one or more metal wires extending spirally in a second direction about the longitudinal axis, the second direction being counter to the first direction, wherein the one or more metal wires intersect the one or more polymer wires at a plurality of intersection points, the one or more metal wires only intersecting the one or more polymer wires such that the one or more metal wires do not form a closed current loop.

39. The expandable stent of claim 38, wherein the plasma comprises a cold oxygen plasma.

40. The expandable stent of claim 38, wherein at least a portion of the polymer wire is coated with a plastic.

41. An expandable stent, comprising:
a plurality of polymer wires spirally extending along a first direction about a longitudinal axis of the expandable stent, the plurality of polymer wires includes an inner wire positioned on an inner surface of the expandable stent and an outer wire positioned on an outer surface of the expandable stent; and
one or more metal wires extending spirally in a second direction about the longitudinal axis, the second direction being counter to the first direction, wherein the one or more metal wires intersect the plurality of polymer wires at a plurality of intersection points, the one or more metal wires only intersecting the one or more polymer wires such that the one or more metal wires do not form a closed current loop.

42. The expandable stent of claim 41, wherein the inner wire is fused to the outer wire.

* * * * *

UNITED STATES PATENT AND TRADEMARK OFFICE
CERTIFICATE OF CORRECTION

PATENT NO. : 7,632,299 B2  Page 1 of 1
APPLICATION NO. : 10/762815
DATED : December 15, 2009
INVENTOR(S) : Jan Weber It is certified that error appears in the above-identified patent and that said Letters Patent is hereby corrected as shown below:

Title page, item (*) Notice:  should read as follows:  Subject to any disclaimer, the term of this patent is extended or adjusted under 35 U.S.C. 154(b) by 1278 days.

Column 10, line 21-22, (Claim 10) please delete "The expandable stent of claim 11, wherein the polymer wire is treated with a plasma." and insert --The expandable stent of claim 11, wherein the polymer wire has a modulus of elasticity between about 10 GPa and about 80 GPa.--, therefore.

Column 11, line 5 (Claim 58) after "polymer" please insert --wire--.

Column 11, line 7 (Claim 59) please delete "25" and insert --33,--, therefore.

Signed and Sealed this

Twentieth Day of July, 2010

David J. Kappos
*Director of the United States Patent and Trademark Office*